United States Patent
Anthis

(10) Patent No.: US 9,090,641 B2
(45) Date of Patent: Jul. 28, 2015

(54) PRECURSORS AND METHODS FOR THE SELECTIVE DEPOSITION OF COBALT AND MANGANESE ON METAL SURFACES

(71) Applicant: Applied Materials, Inc., Santa Clara, CA (US)

(72) Inventor: Jeffrey W. Anthis, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 245 days.

(21) Appl. No.: 13/780,939

(22) Filed: Feb. 28, 2013

(65) Prior Publication Data

US 2013/0236657 A1  Sep. 12, 2013

Related U.S. Application Data

(60) Provisional application No. 61/608,901, filed on Mar. 9, 2012.

(51) Int. Cl.
*C07F 15/06* (2006.01)
*C07F 13/00* (2006.01)
*C23C 16/04* (2006.01)
*C23C 16/18* (2006.01)
*C23C 16/455* (2006.01)
*C07D 277/28* (2006.01)

(52) U.S. Cl.
CPC ............. *C07F 15/065* (2013.01); *C07F 13/005* (2013.01); *C23C 16/04* (2013.01); *C23C 16/18* (2013.01); *C23C 16/45553* (2013.01); *C07D 277/28* (2013.01)

(58) Field of Classification Search
CPC ............................ C07F 13/005; C07F 15/065
See application file for complete search history.

(56) References Cited

PUBLICATIONS

"Mixed [Pyrroles-2-Aldiminate]/[Cyclopentadienyl] Transition Metal Precursors for Deposition of Transition Metal Containing Films for Various Applications", 2009, 9 pages.

*Primary Examiner* — Joseph Kosack
(74) *Attorney, Agent, or Firm* — Servilla Whitney LLC

(57) ABSTRACT

Provided are metal coordination complexes comprising a pyrrole or imidazole-based ligands and cobalt or manganese. Also provided are methods for the selective deposition of cobalt and/or manganese films on metal surfaces using these metal coordination complexes comprising a pyrrole or imidazole-based ligand.

17 Claims, 1 Drawing Sheet

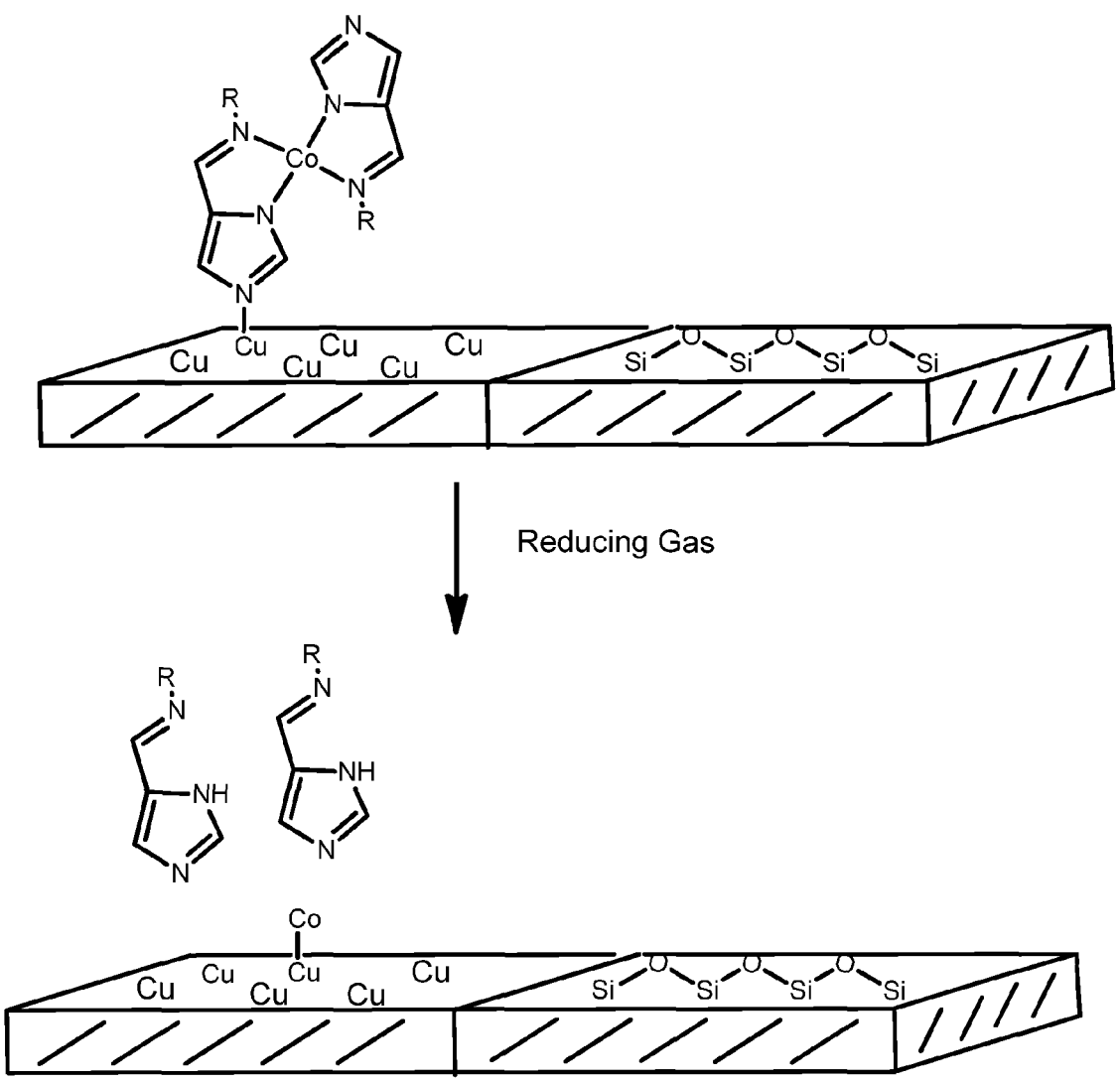

PRECURSORS AND METHODS FOR THE SELECTIVE DEPOSITION OF COBALT AND MANGANESE ON METAL SURFACES

CROSS-REFERENCE TO RELATED APPLICATIONS

This application claims priority to U.S. Provisional Application No. 61/608,901, filed Mar. 9, 2012, the entire contents of which are herein incorporated by reference.

TECHNICAL FIELD

The present invention relates generally to methods of selectively depositing thin films of elemental metal and to metal coordination complexes useful in such methods. In particular, the invention relates to coordination complexes selective for the deposition of elemental cobalt or manganese onto metal onto metal surfaces.

BACKGROUND

Deposition of thin films on a substrate surface is an important process in a variety of industries including semiconductor processing, diffusion barrier coatings and dielectrics for magnetic read/write heads. In the semiconductor industry, in particular, miniaturization requires atomic level control of thin film deposition to produce conformal coatings on high aspect structures. One method for deposition of thin films with atomic layer control and conformal deposition is atomic layer deposition (ALD), which employs sequential, surface reactions to form layers of precise thickness controlled at the Angstrom or monolayer level. Most ALD processes are based on binary reaction sequences which deposit a binary compound film. Each of the two surface reactions occurs sequentially, and because they are self-limiting, a thin film can be deposited with atomic level control. Because the surface reactions are sequential, the two gas phase reactants are not in contact, and possible gas phase reactions that may form and deposit particles are limited. The self-limiting nature of the surface reactions also allows the reaction to be driven to completion during every reaction cycle, resulting in films that are continuous and pinhole-free.

ALD has been used to deposit metals and metal compounds on substrate surfaces. $Al_2O_3$ deposition is an example of a typical ALD process illustrating the sequential and self-limiting reactions characteristic of ALD. $Al_2O_3$ ALD conventionally uses trimethylaluminum (TMA, often referred to as reaction "A" or the "A" precursor) and $H_2O$ (often referred to as the "B" reaction or the "B" precursor). In step A of the binary reaction, hydroxyl surface species react with vapor phase TMA to produce surface-bound $AlOAl(CH_3)_2$ and $CH_4$ in the gas phase. This reaction is self-limited by the number of reactive sites on the surface. In step B of the binary reaction, $AlCH_3$ of the surface-bound compound reacts with vapor phase $H_2O$ to produce AlOH bound to the surface and $CH_4$ in the gas phase. This reaction is self-limited by the finite number of available reactive sites on surface-bound $AlOAl(CH_3)_2$. Subsequent cycles of A and B, purging gas phase reaction products and unreacted vapor phase precursors between reactions and between reaction cycles, produces $Al_2O_3$ growth in an essentially linear fashion to obtain the desired film thickness.

While perfectly saturated monolayers are often desired, this goal is very difficult to achieve in practice. The typical approach to further ALD development has been to determine whether or not currently available chemistries are suitable for ALD. Prior art processes for ALD have been most effective for deposition of metal oxide and metal nitride films. Although a few processes have been developed that are effective for deposition of elemental ruthenium and other late transition metals, there is a need for new elemental metal deposition chemistries that are commercially viable.

Additionally, during the manufacture of integrated circuits, there is often a need to deposit metal films onto other metal surfaces, but avoid depositing metal onto exposed dielectric regions. For example, there may be copper on the bottom of a via that has low-k dielectric sidewalls. In order to complete fabrication of the integrated circuits, it is necessary to deposit a metal over the existing copper metal areas, but avoid the dielectric areas. Thus, there is a need for a method of deposition that is selective for metals, and will avoid such deposition onto the exposed dielectric regions.

The present invention addresses these problems by providing novel chemistries which are specifically designed and optimized to take advantage of the atomic layer deposition process. In fact, before the present invention, there were no known commercially acceptable atomic layer deposition precursors that are capable of selectively depositing cobalt and/or manganese onto metal surfaces.

SUMMARY

One aspect of the invention relates to a metal coordination complex comprising a structure represented by one of:

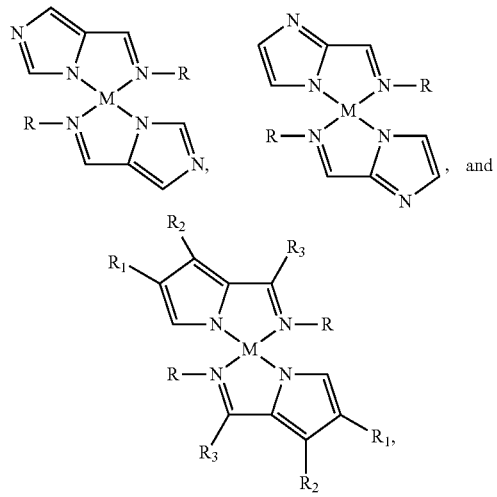

wherein R is hydrogen or any C1-C6 alkyl group, $R_1$, $R_2$ or $R_3$ are independently selected from isonitrile or nitrile, and M is selected from cobalt and manganese. Thus, in one or more embodiments, the metal coordination complex of claim 1, wherein the metal coordination complex has a structure represented by one of:

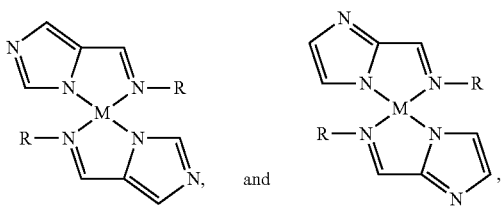

wherein R is hydrogen or any C1-C6 alkyl group and M is selected from cobalt and manganese. In one variant, R is isopropyl. In one or more other embodiments, the metal coordination complex of claim 1, wherein the metal coordination complex has a structure represented by:

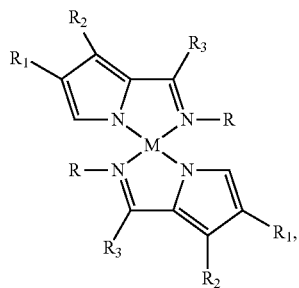

wherein R is hydrogen or any C1-C6 alkyl group, $R_1$, $R_2$ or $R_3$ are independently selected from isonitrile or nitrile, and M is selected from cobalt and manganese. Again, in one variant of these embodiments, R is isopropyl.

Another aspect of the invention relates to a method of selectively depositing a metal film. The method comprises contacting a substrate surface, wherein the substrate surface comprises a metal region and a dielectric region, with a vapor phase metal coordination complex having a structure represented by one of

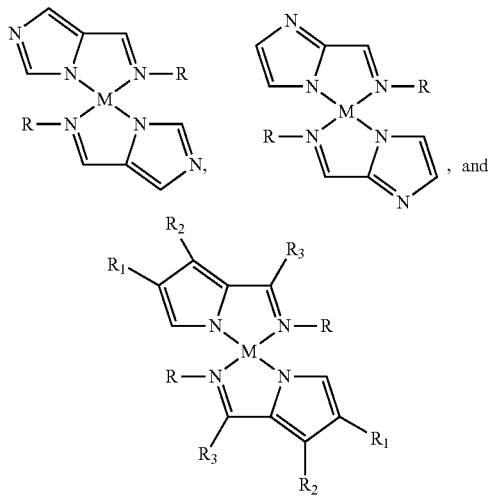

wherein R is hydrogen or any C1-C6 alkyl group, $R_1$, $R_2$ or $R_3$ are independently selected from isonitrile or nitrile, and M is selected from cobalt and manganese, such that a layer is formed on the metal region, but not the dielectric region, and the layer formed comprises the metal coordination complex bound to the metal surface, and contacting the bound metal complex with a reducing gas such that an exchange reaction occurs between the bound metal coordination complex and the reducing gas, thereby dissociating the bound metal complex and producing a first layer of elemental cobalt or manganese on the metal region substrate surface. In one or more embodiments of this method, the metal surface comprises one or more of copper and cobalt. In one or more other embodiments, the dielectric comprises $SiO_2$. In one or more other embodiments, the reducing gas comprises hydrogen.

In one or more variants, the method can further comprise purging excess unreacted vapor phase metal complex with an inert gas prior to addition of the reducing gas. In other variants, the method can further comprise exposing the layer of elemental cobalt or manganese to a plasma. In specific embodiments, the plasma is a remote plasma comprising hydrogen. In yet other embodiments, the method further comprises contacting the first layer of elemental manganese or cobalt on the metal region of the substrate surface with the vapor phrase metal coordination complex such that an exchange reaction occurs between the metal complex and the first layer of elemental cobalt or manganese, thereby partially dissociating the metal complex and producing a second layer on the surface comprising the partially dissociated metal complex bound to the first elemental manganese or cobalt layer; and contacting the bound metal complex of the second layer with a reducing gas such that an exchange reaction occurs between the bound metal complex and the reducing gas, thereby dissociating the bound metal complex and producing a second layer of elemental manganese or cobalt on the metal region substrate surface.

A third aspect of the invention also relates to a method of depositing a metal film. The method comprises contacting a substrate comprising a metal surface with a vapor phase metal coordination complex having a structure represented by one of:

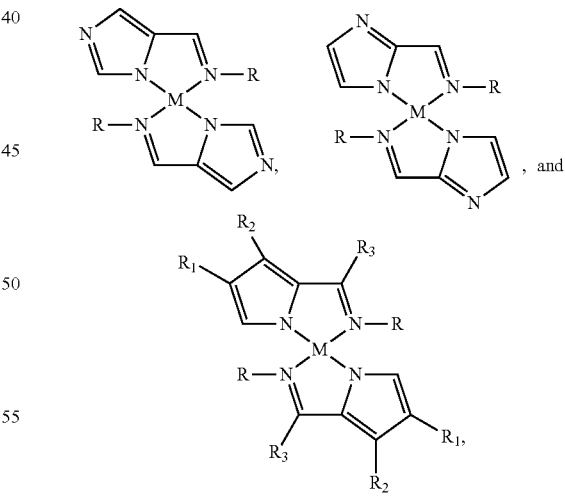

wherein R is hydrogen or any C1-C6 alkyl group, $R_1$, $R_2$ or $R_3$ are independently selected from isonitrile or nitrile, and M is selected from cobalt and manganese, such that a layer is formed on the metal surface, and the layer formed comprises the metal coordination complex bound to the metal surface; and contacting the bound metal complex with a reducing gas such that an exchange reaction occurs between the bound metal coordination complex and the reducing gas, thereby dissociating the bound metal complex and producing a first layer of elemental cobalt or manganese on the metal surface.

In one or more embodiments of this aspect, the metal surface comprises one or more of copper and cobalt. In one or more other embodiments, the substrate further comprises a non-metal surface, and the metal coordination complex does not coordinate to the non-metal surface. In specific embodiments the non-metal surface comprises a dielectric.

In one or more embodiments, the method may further comprise purging excess unreacted vapor phase metal complex with an inert gas prior to addition of the reducing gas. In other embodiments, the method further comprises exposing the layer of elemental cobalt or manganese to a plasma. In yet still other embodiments, the method can further comprise contacting the first layer of elemental manganese or cobalt on the metal region of the substrate surface with the vapor phrase metal coordination complex such that an exchange reaction occurs between the metal complex and the first layer of elemental cobalt or manganese, thereby partially dissociating the metal complex and producing a second layer on the surface comprising the partially dissociated metal complex bound to the first elemental manganese or cobalt layer; and contacting the bound metal complex of the second layer with a reducing gas such that an exchange reaction occurs between the bound metal complex and the reducing gas, thereby dissociating the bound metal complex and producing a second layer of elemental manganese or cobalt on the metal region substrate surface.

BRIEF DESCRIPTION OF THE DRAWINGS

The FIGURE is an illustration of a selective ALD process using a representative metal coordination complex according to the invention.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways. It is also to be understood that the complexes and ligands of the present invention may be illustrated herein using structural formulas which have a particular stereochemistry. These illustrations are intended as examples only and are not to be construed as limiting the disclosed structure to any particular stereochemistry. Rather, the illustrated structures are intended to encompass all such complexes and ligands having the indicated chemical formula.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

The term "metal coordination complex" as used herein is used interchangeably with "metal complex" and "coordination complex," and includes structures that consist of a central metal atom bonded to one or more ligands. As will be discussed in more detail below, the metal complexes of the invention comprise pyrrole or imidazole-based ligands bonded to metals.

One aspect of the invention relates to ligands useful for forming a metal coordination complex, which may be a member of one of three groups of structurally related compounds. The ligands have a preferential eta-2-bonding mode to a Co or Mn metal center through nitrogen bonds in a pyrrolyl-imine structure, and an ancillary group, either incorporated into the pyrrolyl ring or off of one of the carbon groups either in the ring or on the pendant imine carbon. In one or more embodiments, the pyrrolyl group may have a second nitrogen incorporated into the ring to make it an imidizolyl group or a pendant group which will have high affinity to Cu metal, such as nitrile or isonitrile attached to the ring or bonded to the imine carbons. These ligands have ancillary moieties that help the metal coordination complex preferentially bond to metal surfaces. The precursors selectively adsorb to a metal surface because of the reactivity of the nitrogen, nitrile or isonitrile that is not involved in bonding to the precursor metal.

A first such group of ligands is may be represented by formula (I):

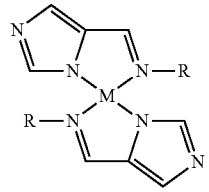

wherein R is hydrogen or any C1-C6 alkyl group and M is selected from cobalt and manganese. In one embodiment, R is isopropyl.

A second such group of ligands may be represented by formula (II):

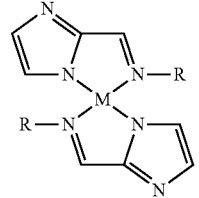

wherein R is hydrogen or any C1-C6 alkyl group and M is selected from cobalt and manganese. In one embodiment, R is isopropyl.

A third such group of ligands may be represented by formula (III):

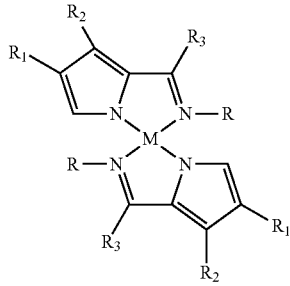

wherein R is hydrogen or any C1-C6 alkyl group, $R_1$, $R_2$ or $R_3$ are independently selected from isonitrile or nitrile, and M is selected from cobalt and manganese. In one embodiment, R is isopropyl.

The coordination complexes according to one or more embodiments of the invention may be synthesized according to chemical schematic 1 below. Other variants of the metal coordination complexes described herein may be synthesized by using the appropriate analogous starting reagents.

Schematic 1: Synthesis of the Coordination Complexes

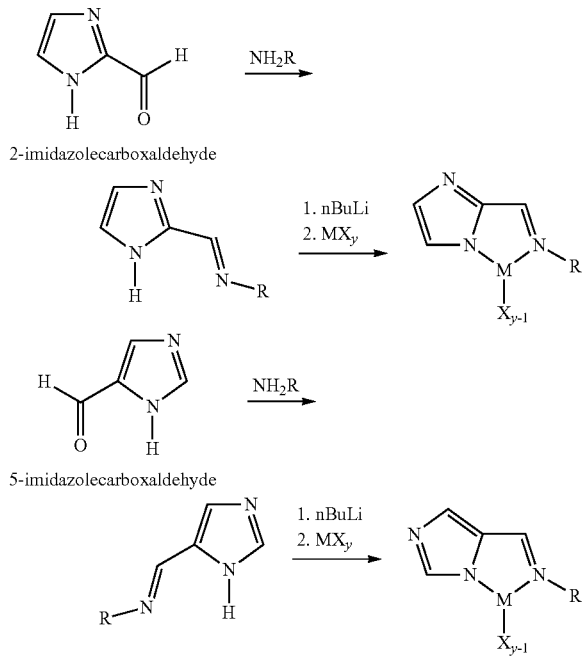

2-imidazolecarboxaldehyde 5-imidazolecarboxaldehyde

Another aspect of the invention relates to a method of selectively depositing a metal film. The method comprises contacting a substrate surface, wherein the substrate surface comprises a metal region and a dielectric region, with a vapor phase metal coordination complex having a structure represented by formulae (I), (II), or (III):

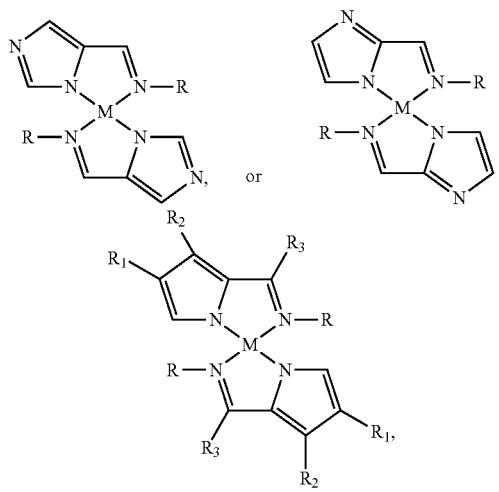

wherein R is hydrogen or any C1-C6 alkyl group, $R_1$, $R_2$ or $R_3$ are independently selected from isonitrile or nitrile, and M is selected from cobalt or manganese, such that a layer is formed on the metal region, but not the dielectric region, and the layer formed comprises the metal coordination complex bound to the metal surface; and contacting the bound metal complex with a reducing gas such that an exchange reaction occurs between the bound metal coordination complex and the reducing gas, thereby dissociating the bound metal complex and producing a first layer of elemental cobalt or manganese on the metal region substrate surface.

In one or more embodiments, the reducing gas comprises hydrogen. The method may also further comprise purging excess unreacted vapor phase metal complex with an inert gas prior to addition of the reducing gas. In other embodiments, the method may further comprise exposing the layer of elemental cobalt or manganese to a plasma. Such a plasma treatment can be used to remove carbon or nitrogen that remains from the deposition process. In several embodiments, plasma treatment can be done every deposition or every few depositions. For example, the deposited film may be exposed to a plasma every second, third, fourth, fifth or sixth deposition cycles. In further embodiments, the plasma may be a remote plasma, and/or the plasma may comprise hydrogen.

In the illustrative example of such a process shown in the FIGURE, the metal coordination complex used is represented by formula (I), with a cobalt metal center. The metal coordination complex is vaporized, optionally in a mixture with an inert carrier gas, and then flowed in the vapor phase to a substrate within a deposition chamber (not shown). The substrate has one region that is a metal surface, in this case copper, and another non-metal surface. In the FIGURE, the non-metal surface is a dielectric, namely $SiO_2$. Because of the affinity of the ligand to copper or cobalt metal surfaces, the metal coordination complex coordinates to the metal surface, but not the dielectric surface. Although not wishing to be bound to any particular theory, it is thought that the metal coordination complex coordinates through at least one of its ligands, as shown in the FIGURE. Accordingly, the precursor selectively adsorbs to the copper metal surface. The surface is exposed to the metal coordination complex for sufficient time to permit adsorption of the complex in a layer on the surface. A reducing precursor/gas is then flowed into the deposition chamber to reduce the bond(s) in the ligand, releasing the ligands from the metal center and leaving an atomic layer of elemental metal, cobalt, on the substrate.

Additional layers may be added. The deposited manganese and cobalt surfaces will further react with the precursors to continue to grow a thicker film. The precursors will still preferentially deposit over the metal surface, rather than over the dielectric surface. Thus, in one or more embodiments, the method further comprises contacting the first layer of elemental manganese or cobalt on the metal region of the substrate surface with the vapor phrase metal coordination complex such that an exchange reaction occurs between the metal complex and the first layer of elemental cobalt or manganese, thereby partially dissociating the metal complex and producing a second layer on the surface comprising the partially dissociated metal complex bound to the first elemental manganese or cobalt layer; and contacting the bound metal complex of the second layer with a reducing gas such that an exchange reaction occurs between the bound metal complex and the reducing gas, thereby dissociating the bound metal complex and producing a second layer of elemental manganese or cobalt on the metal region substrate surface.

Yet another aspect of the invention also relates to a method of depositing a metal film. The method comprises contacting a substrate comprising a metal surface with a vapor phase metal coordination complex having a structure represented by formulae (I), (II) or (III):

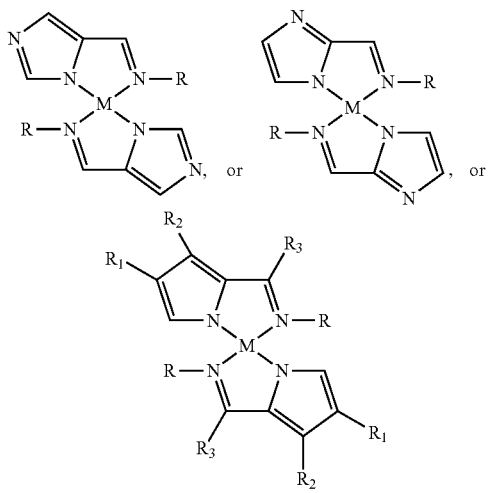

wherein R is hydrogen or any C1-C6 alkyl group, $R_1$, $R_2$ or $R_3$ are independently selected from isonitrile or nitrile, and M is selected from cobalt and manganese, such that a layer is formed on the metal surface, and the layer formed comprises the metal coordination complex bound to the metal surface; and contacting the bound metal complex with a reducing gas such that an exchange reaction occurs between the bound metal coordination complex and the reducing gas, thereby dissociating the bound metal complex and producing a first layer of elemental cobalt or manganese on the metal surface. In one or more embodiments, the metal surface comprises one or more of copper and cobalt.

In one or more embodiments, the substrate surface further comprises a non-metal surface, and the metal coordination complex does not coordinate to the non-metal surface. In further embodiments, the non-metal surface comprises a dielectric surface. Additionally, in other embodiments, the dielectric comprises $SiO_2$.

In one or more embodiments, the reducing gas comprises hydrogen. The method may also further comprise purging excess unreacted vapor phase metal complex with an inert gas prior to addition of the reducing gas. In other embodiments, the method may further comprise exposing the layer of elemental cobalt or manganese to a plasma. In further embodiments, the plasma may be a remote plasma, and/or the plasma may comprise hydrogen.

Additional layers may be added. Thus, in one or more embodiments, the method further comprises contacting the first layer of elemental manganese or cobalt on the metal region of the substrate surface with the vapor phrase metal coordination complex such that an exchange reaction occurs between the metal complex and the first layer of elemental cobalt or manganese, thereby partially dissociating the metal complex and producing a second layer on the surface comprising the partially dissociated metal complex bound to the first elemental manganese or cobalt layer; and contacting the bound metal complex of the second layer with a reducing gas such that an exchange reaction occurs between the bound metal complex and the reducing gas, thereby dissociating the bound metal complex and producing a second layer of elemental manganese or cobalt on the substrate surface. If there are non-metal regions, such as a dielectric, deposition will preferentially occur over the metal region.

In another embodiment, a method of selectively forming cobalt and/or manganese metal on a substrate surface comprises: during an atomic layer deposition process, exposing a substrate with a metal region and non-metal region to a vapor phase metal coordination complex having at least one of the formulae (I), (II), and/or (III), such that a layer is selectively formed on the metal region of the substrate surface comprising the metal coordination complex bound to the surface by a ligand; during an atomic layer deposition process, exposing the substrate having bound metal complex with a reducing gas such that an exchange reaction occurs between the bound metal coordination complex and the reducing gas, thereby dissociating the bound metal complex and producing a first layer of cobalt and/or manganese on the metal region of the substrate surface, but not the non-metal region; and sequentially repeating the atomic layer deposition process and the treatment.

Yet another embodiment of the invention relates to a method of selectively forming manganese and/or cobalt on a substrate surface, comprising: (a) disposing a substrate with a metal surface within a process chamber; (b) flowing a vapor phase metal coordination complex having at least one of the formulae (I), (II) and/or (III), such that a layer is selectively formed on the metal substrate surface, the layer comprising the metal coordination complex bound to the surface; (c) purging the process chamber; (d) flowing a reducing gas such that an exchange reaction occurs between the bound metal coordination complex and the reducing gas, thereby dissociating the bound metal complex and producing a first layer of manganese and/or cobalt on the metal surface of the substrate, but not the non-metal surface; (e) purging the process chamber; repeating (a) through (e). In one or more embodiments, the substrate also comprises a non-metal surface, such as a dielectric layer, and the cobalt and/or manganese film is preferentially deposited onto the metal surface over the non-metal surface.

The substrate for deposition of the elemental thin layer films may be any substrate suitable for conformal film coating in an ALD or CVD process, which contains a metal surface. As discussed above, the metal region may comprise copper and/or cobalt. In one aspect of the invention, the substrate is a semiconductor substrate. The substrate may also comprise a non-metal surface onto which the metal will not be deposited. Such non-metal substrate surfaces include, for example, silicon, silica or coated silicon.

As briefly discussed above, additional layers of elemental metal may optionally be selectively formed added on the first atomic layer by repeating the process of the reaction cycle. Hydrogen remaining from the preceding reduction reaction is purged from the deposition chamber using an inert gas and a metal coordination complex in vapor phase is again flowed into the chamber into contact with the metal film on the substrate surface. An exchange reaction occurs between the metal coordination complex in the vapor phase and the metal atoms on the metal of the first atomic layer. This displaces one of the ligands from the vapor phase metal coordination complex and leaves the ligand of the metal coordination complex bound to the metal atom of the first atomic layer. However, the coordination complex again does not coordinate to any non-metal region of the substrate surface that is present.

The reaction time, temperature and pressure are selected to create a metal-surface interaction and form a layer on the surface of the substrate. However, the temperature selected should be a temperature lower than the decomposition temperature of the precursors. In some embodiments, the temperature is selected to be relatively high; that is, just below the decomposition temperature. Unreacted vapor phase metal coordination complex and released ligand are purged from the deposition chamber using an insert gas. A reducing gas is flowed into the deposition chamber to reduce the bond(s)

between the metal and any remaining ligand(s), releasing the remaining ligand(s) from the metal center and producing a second atomic layer of cobalt and/or manganese on the first atomic layer of elemental metal, but not on the non-metal region of the substrate surface.

Thus, in one embodiment, a second layer of manganese and/or cobalt may be added by contacting the substrate surface with the first layer of elemental manganese and/or cobalt with the vapor phrase metal coordination complex such that an exchange reaction occurs between the metal complex and the first layer of elemental metal, thereby partially dissociating the metal complex and producing a second layer on the surface comprising the partially dissociated metal complex bound to the first cobalt and/or manganese layer; and contacting the bound metal complex of the second layer with a reducing gas such that an exchange reaction occurs between the bound metal complex and the reducing gas, thereby dissociating the bound metal complex and producing a second layer of cobalt and/or manganese on the surface of the substrate. Because of the preferential affinity of the ligands to metal surfaces, the metal complex will again not coordinate to the non-metal region of the substrate surface. Additional repetitions of the deposition cycle may be used to build a film of the desired thickness.

The reaction conditions for the ALD reaction will be selected based on the properties of the selected metal coordination complex. The deposition can be carried out at atmospheric pressure but is more commonly carried out at a reduced pressure. The vapor pressure of the metal coordination complex should be low enough to be practical in such applications. The substrate temperature should be high enough to keep the bonds between the metal atoms at the surface intact and to prevent thermal decomposition of gaseous reactants. However, the substrate temperature should also be high enough to keep the source materials (i.e., the reactants) in the gaseous phase and to provide sufficient activation energy for the surface reaction. The appropriate temperature depends on the specific metal coordination complex used and the pressure. The properties of a specific metal coordination complex for use in the ALD deposition methods of the invention can be evaluated using methods known in the art, allowing selection of appropriate temperature and pressure for the reaction. In general, lower molecular weight and the presence of functional groups that increase the rotational entropy of the ligand sphere result in a melting point that yields liquids at typical delivery temperatures and increased vapor pressure.

An optimized metal coordination complex having formula (I), (II), or (III) for use in the deposition methods of the invention will have all of the requirements for sufficient vapor pressure, sufficient thermal stability at the selected substrate temperature and sufficient reactivity to produce a reaction on the surface of the substrate without unwanted impurities in the thin film or condensation. Sufficient vapor pressure ensures that molecules of the source compound are present at the substrate surface in sufficient concentration to enable a complete self-saturating reaction. Sufficient thermal stability ensures that the source compound will not be subject to the thermal decomposition which produces impurities in the thin film.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A metal coordination complex comprising a structure represented by one of:

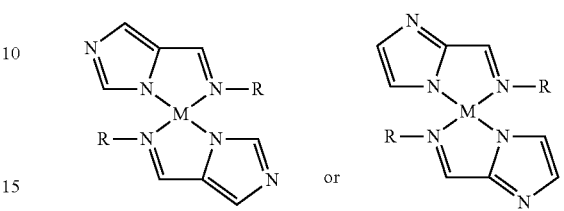

wherein R is hydrogen or any C1-C6 alkyl group and M is selected from cobalt and manganese.

2. The metal coordination complex of claim 1, wherein R is isopropyl.

3. A method of selectively depositing a metal film, the method comprising:
   contacting a substrate surface, wherein the substrate surface comprises a metal region and a dielectric region, with a vapor phase metal coordination complex having a structure represented by one of

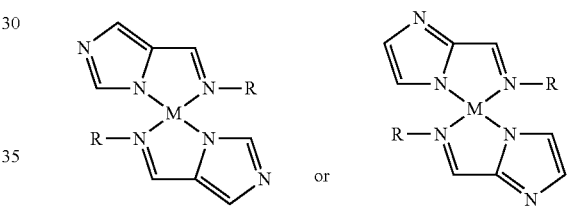

wherein R is hydrogen or any C1-C6 alkyl group and M is selected from cobalt and manganese, such that a layer is formed on the metal region, but not the dielectric region, and the layer formed comprises the metal coordination complex bound to the metal surface; and
   contacting the bound metal complex with a reducing gas such that an exchange reaction occurs between the bound metal coordination complex and the reducing gas, thereby dissociating the bound metal complex and producing a first layer of elemental cobalt or manganese on the metal region substrate surface.

4. The method of claim 3, wherein the metal surface comprises one or more of copper and cobalt.

5. The method of claim 3, wherein the dielectric comprises $SiO_2$.

6. The method of claim 3, wherein the reducing gas comprises hydrogen.

7. The method of claim 3, further comprising purging excess unreacted vapor phase metal complex with an inert gas prior to addition of the reducing gas.

8. The method of claim 3, further comprising exposing the layer of elemental cobalt or manganese to a plasma.

9. The method of claim 8, wherein the plasma is a remote plasma comprising hydrogen.

10. The method of claim 3, the method further comprising:
   contacting the first layer of elemental manganese or cobalt on the metal region of the substrate surface with the vapor phrase metal coordination complex such that an exchange reaction occurs between the metal complex and the first layer of elemental cobalt or manganese, thereby partially dissociating the metal complex and producing a second layer on the surface comprising the partially dissociated metal complex bound to the first elemental manganese or cobalt layer; and contacting the bound metal complex of the second layer with a reducing gas such that an exchange reaction occurs between the bound metal complex and the reducing gas, thereby dissociating the bound metal complex and producing a second layer of elemental manganese or cobalt on the metal region substrate surface.

11. A method of depositing a metal film, the method comprising:

contacting a substrate comprising a metal surface with a vapor phase metal coordination complex having a structure represented by one of:

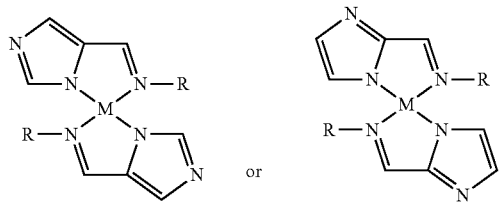

wherein R is hydrogen or any C1-C6 alkyl group and M is selected from cobalt and manganese, such that a layer is formed on the metal surface, and the layer formed comprises the metal coordination complex bound to the metal surface; and contacting the bound metal complex with a reducing gas such that an exchange reaction occurs between the bound metal coordination complex and the reducing gas, thereby dissociating the bound metal complex and producing a first layer of elemental cobalt or manganese on the metal surface.

12. The method of claim 11, wherein the metal surface comprises one or more of copper and cobalt.

13. The method of claim 11, wherein the substrate further comprises a non-metal surface, and the metal coordination complex does not coordinate to the non-metal surface.

14. The method of claim 11, wherein the non-metal surface comprises a dielectric.

15. The method of claim 11, further comprising purging excess unreacted vapor phase metal complex with an inert gas prior to addition of the reducing gas.

16. The method of claim 11, further comprising exposing the layer of elemental cobalt or manganese to a plasma.

17. The method of claim 11, the method further comprising:

contacting the first layer of elemental manganese or cobalt on the metal region of the substrate surface with the vapor phrase metal coordination complex such that an exchange reaction occurs between the metal complex and the first layer of elemental cobalt or manganese, thereby partially dissociating the metal complex and producing a second layer on the surface comprising the partially dissociated metal complex bound to the first elemental manganese or cobalt layer; and contacting the bound metal complex of the second layer with a reducing gas such that an exchange reaction occurs between the bound metal complex and the reducing gas, thereby dissociating the bound metal complex and producing a second layer of elemental manganese or cobalt on the metal region substrate surface.

* * * * *